US007061255B1

(12) United States Patent
Foreman et al.

(10) Patent No.: US 7,061,255 B1
(45) Date of Patent: Jun. 13, 2006

(54) CORROSION MONITORING SYSTEM

(75) Inventors: Donald S. Foreman, Fridley, MN (US);
Russ A. Braunling, Eden Praire, MN (US); Darryl J. Wrest, O'Fallon, MO (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/997,369

(22) Filed: Nov. 24, 2004

(51) Int. Cl.
*G01R 27/08* (2006.01)
(52) U.S. Cl. ............... 324/700; 324/691; 324/603; 204/404
(58) Field of Classification Search ............ 324/700, 324/691, 603; 204/404
See application file for complete search history.

(56) References Cited

U.S. PATENT DOCUMENTS

| 4,217,544 | A | * | 8/1980 | Schmidt | 324/721 |
| 4,498,044 | A | * | 2/1985 | Horn | 324/691 |
| 4,587,479 | A | * | 5/1986 | Rhoades et al. | 324/700 |
| 5,446,369 | A | * | 8/1995 | Byrne et al. | 324/71.2 |
| 5,854,557 | A | * | 12/1998 | Tiefnig | 324/700 |
| 6,831,469 | B1 | * | 12/2004 | Foreman et al. | 324/691 |

\* cited by examiner

*Primary Examiner*—Anjan Deb
*Assistant Examiner*—John Zhu
(74) *Attorney, Agent, or Firm*—Kris T. Fredrick

(57) ABSTRACT

A system for monitoring corrosion in metal by comparing a test sample exposed to a corrosion causing environment and a reference sample exposed to a protected environment. An AC voltage source generates a square wave signal oscillating between ground and voltage Vcc and a filter is positioned to filter the signal to produce a sine wave with no second harmonic component. A voltage-driven current source and inverting amplifier produce a current referenced to 0.5 Vcc to provide an AC current from the drive voltage driven sinusoidally and symmetrically above and below 0.5 Vcc. A transformer steps up the AC current and thereafter transmits the current through the samples to an amplifier for amplifying the current to provide outputs in a ratio representing the degree of corrosion of the reference sample. The system can operate in situ for on site measurement and uses relatively low current to permit long operation.

20 Claims, 2 Drawing Sheets

CORROSION MONITORING SYSTEM

FIELD OF THE INVENTION

The present invention relates in general to a system for measuring corrosion in materials by comparison of a material being corroded with an essentially identical material in a protected environment. More particularly, the present invention relates to a system in which AC voltage at low current levels is used to measure corrosion without high energy drain.

BACKGROUND OF THE INVENTION

The use of the electrical resistance technique is widely applied in monitoring material loss occurring in industrial plant equipment and pipelines. This technique operates by measuring the change in electrical resistance of a metallic element immersed in a product media relative to a reference element sealed within the probe body. Since temperature changes affect the resistance of both the exposed and protected element equally, measuring the resistance ratio minimizes the influence of changes in the ambient temperature. If the corrosion occurring in the vessel under study is roughly uniform, a change in resistance is proportional to an increment of corrosion. Although universally applicable, the electrical resistance method is uniquely suited to corrosive environments having either poor or non-continuous electrolytes such as vapors, gases, soils, "wet" hydrocarbons, and non-aqueous liquids.

An electrical resistance monitoring system consists of an instrument usually with data logging functions connected to a probe. The instrument may be permanently installed to provide continuous information, or may be portable to gather periodic data from a number of locations. The probe is equipped with a sensing element having a composition and material processing history similar to that of the process equipment of interest.

Electrochemical noise is a useful, sensitive and non-intrusive technique for corrosion monitoring. Fluctuations of potential or current of a corroding metallic specimen are monitored to gage and understand the corrosion process. Electrochemical noise is used to investigate localized corrosion processes such as pitting or stress corrosion cracking, exfoliation, and erosion-corrosion in either laboratory or diverse and complex industrial environments. During localized corrosion, film formation, passivation breakdown or pit propagation processes generate the electrochemical noise that is observed. The most traditional way to analyze electrochemical noise data has been to transform time records in the frequency domain in order to obtain power spectra with FFT methods.

Inductive resistance probes are similar to ER probes. The weight loss in the sensor element is detected by measuring changes in the inductive resistance of a coil, located inside the element. The inductive measurement technique provides greatly improved sensitivity and earlier detection of corrosion rate changes compared to conventional electrical resistance probes. Inductive resistance probes require temperature compensation, similar to ER probes. Like ER probes, the sensors can be used in a broad range of environments such as low conductivity and non-aqueous environments, where electrochemical techniques are generally unsuitable.

Polarization resistance is particularly useful as a method to rapidly identify corrosion upsets and initiate remedial action, thereby prolonging plant life and minimizing unscheduled downtime. The technique is utilized to maximum effect, when installed as a continuous monitoring system in almost all types of water-based, corrosive environments. The measurement of polarization resistance has very similar requirements to the measurement of full polarization curves.

One drawback all prior art systems and devices have is that the power required to operate them is far too high for sustained, long-term battery operation. The resistances of corroding test coupons are very low, typically on the order of 10 milliohms. Because low average power consumption is a requirement in many applications of corrosion measurement, high-current excitation of the coupons is not an option, while low-current excitation results in signals of microvolt magnitude. Presently available commercial instruments fail to meet the low-power requirement.

Therefore, it would be of great advantage if a system could be invented that would use low-power demand while providing acceptable accuracy.

Another advantage would be if a system could be invented that would avoid offset and thermoelectric potentials at connection points.

Yet another advantage would be a system for measuring corrosion that is more accurate due to elimination of noise and offset from high gain amplification.

Other advantages and features will appear hereinafter.

SUMMARY OF THE INVENTION

The present invention provides a system for monitoring corrosion in metal. A test sample is exposed to a corrosion causing environment and a reference sample is exposed to a protected environment. In its simples form the system of this invention uses an AC current to excite the samples or coupons to avoid DC offset errors in amplifiers. The system uses a 10:1 current step-up transformer in the drive circuit to gain a tenfold increase in power efficiency in driving the very low-impedance load. Very low-noise, low-offset, high-gain instrumentation operational amplifiers are used in the first signal-processing stage. Ratiometric measurement is accomplished by current driving the reference and sensor coupon in series, sensing and signal-processing their responsive voltages, and taking the ratio of these voltages, using conventional digital signal processing, to provide an accurate, in situ measurement of the corrosion of the test sample.

BRIEF DESCRIPTION OF THE DRAWINGS

For a more complete understanding of the invention, reference is hereby made to the drawings, in which.

In the figures, like reference characters designate identical or corresponding components and units throughout the several views.

DETAILED DESCRIPTION OF THE PREFERRED EMBODIMENT

Figure 1:
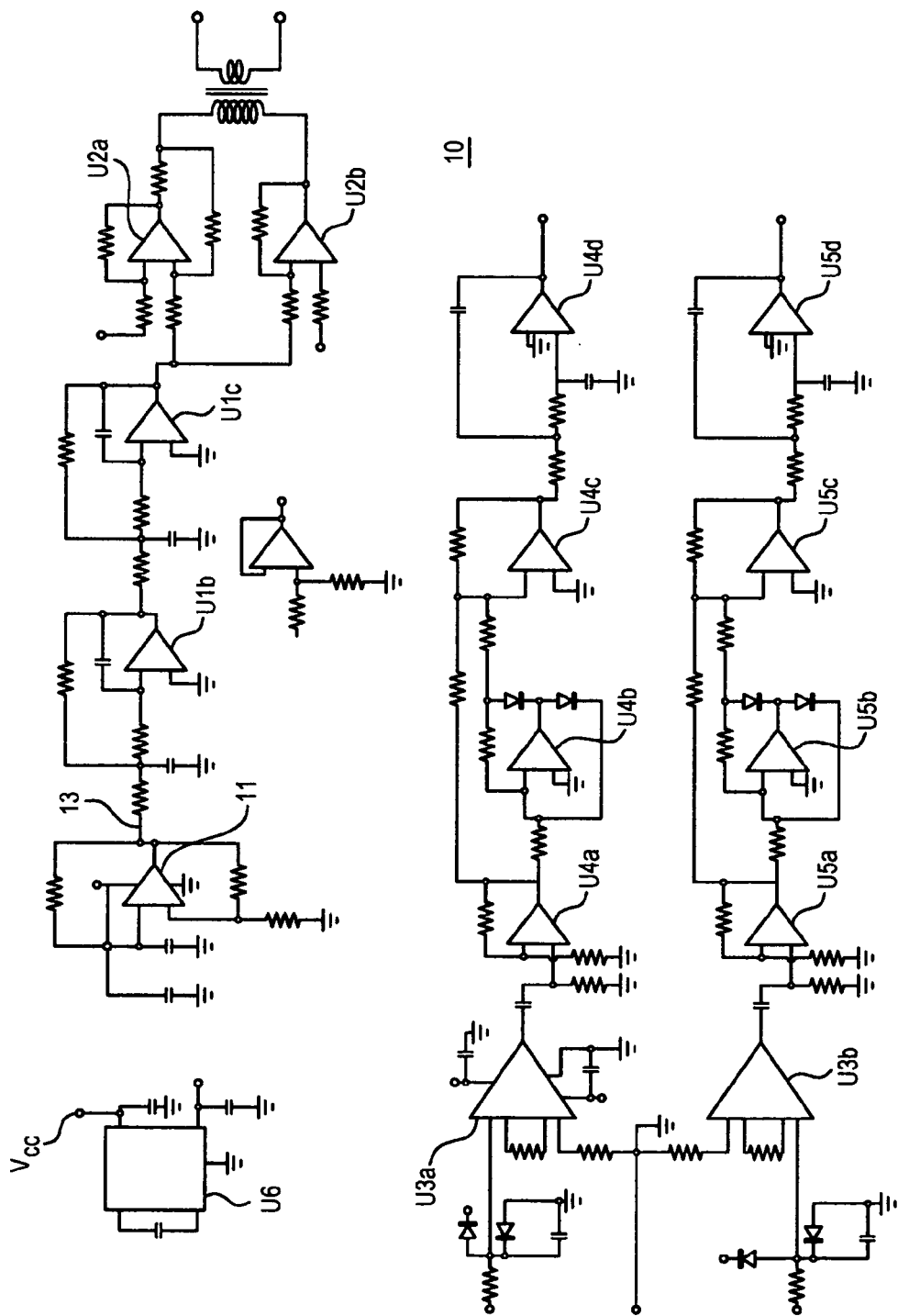
FIG. 1 is a circuit diagram illustrating the operation of a preferred embodiment of the present invention.
Figure 2:
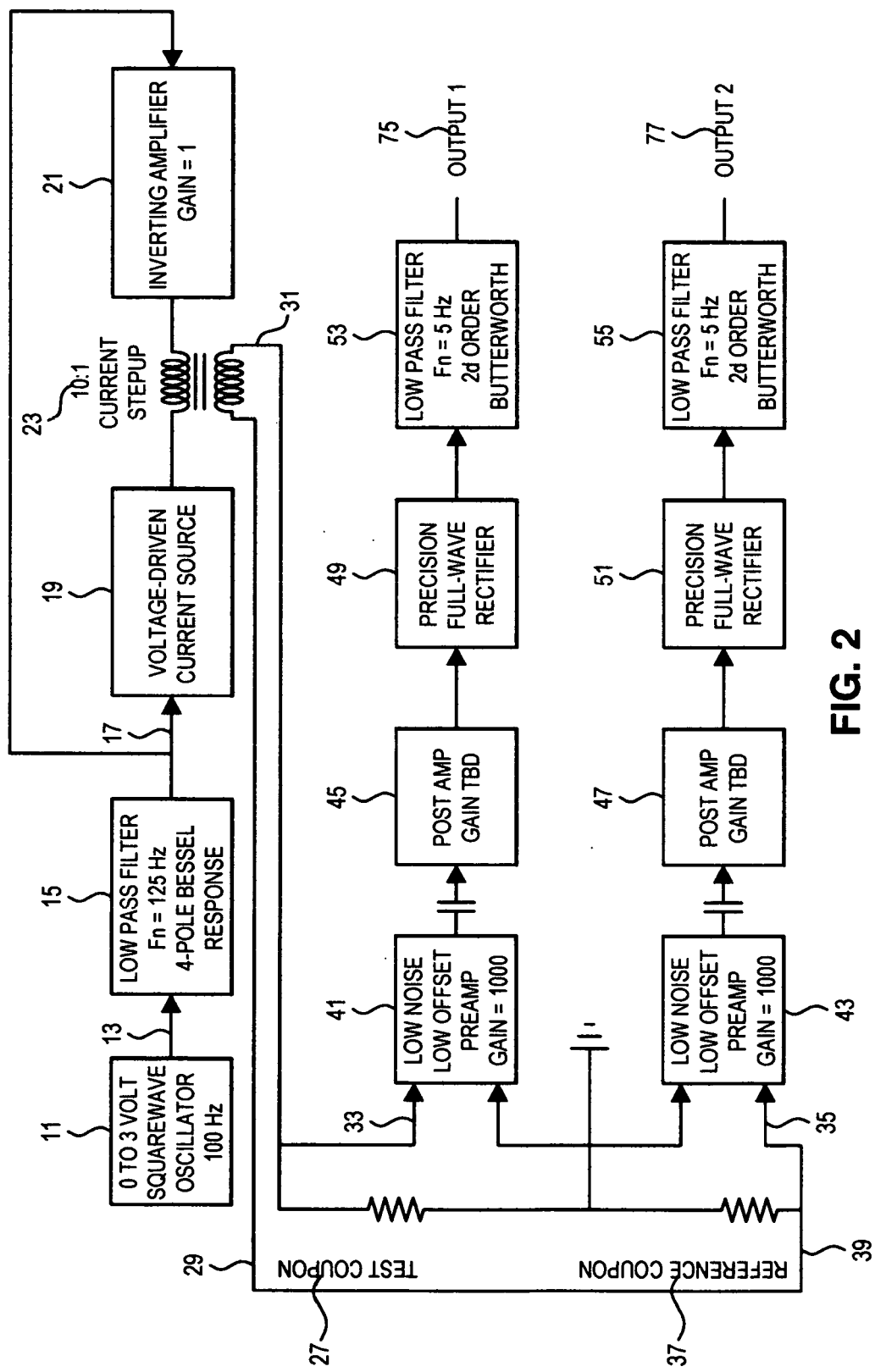
FIG. 2 is a block diagram illustrating a system approach of the present invention.

Referring to the figures, FIG. 1, which is a schematic diagram, and FIG. 2, which is a block flow diagram, showing the system generally at 10 in which the oscillator 11 is a 100 Hz symmetrical hysteretic oscillator using a rail-to-rail input and output that produces a symmetrical square wave 13 oscillating between ground and Vcc. This type of oscillator has the advantage over sine wave oscillators, such as, for example, Wein bridge, state-variable, phase shift or twin-tee oscillators, in that it is capable of starting immediately at full magnitude. It has been found that this is important to minimize the total time required from application of power to availability of stable measurement data. It has been found that post-filtering of such a square wave signal provides much faster response than was possible with alternative oscillators, while also providing acceptable spectral purity.

The resulting square wave 13 is filtered by a $4^{th}$ order Bessel-response low pass filter 15 comprised of U1b, U1c and associated circuitry. The corner frequency of this filter is 125 Hz. The filtered output 17 from filter 15 is a sine wave with no second harmonic component because it is symmetrical. The output from filter 15 also has been found to have less than a 1% third-harmonic component. Filter 15 has been found to have excellent transient response while providing acceptable spectral purity. The output sinusoid 17 is stable to within less than 0.1% of steady state magnitude within less than 200 milliseconds.

The sinusoidal voltage 17 thus produced is presented to a voltage-driven current source 19, comprised of U2a and associated circuitry. It drives its load with a sinusoidal current of 5 mA peak regardless of load impedance or voltage required to produce the intended current. The current source is referenced to ½ Vcc so it provides AC current as the drive voltage varies sinusoidally and symmetrically above and below ½ Vcc.

U2b inverting amplifier 21 inverts the sinusoidal voltage with unity gain. This provides differential drive for the transformer 23 primary. The current drive's output can only vary from near Vcc to near ground, but since the other end of the transformer 23's primary is connected to a voltage source out of phase with the drive current, drive voltage approaches ±Vcc in magnitude if necessary to reach peak values of ±5 mA. The actual voltage appearing on transformer 23's primary will depend on the resistance of the leads to the coupon.

Since the coupons 27 and 37 are current driven in series, they will be excited with identical current via lines 29 and 39. Transformer 23 isolation prevents any possibility of exciting ground loop current in the common return 31.

The sensor and reference coupons are Kelvin connected as shown in FIG. 2. Sense voltage returns on wires 31 separate from those wires 29, 39 conducting the drive current. !00 Hz for the oscillator 11 was chosen as a high enough frequency to result in a transformer 23 of acceptable size and weight (in practice about 2 cm³ and about 4 grams) but low enough to minimize the effects of inductive coupling between drive wires and sense wires, in the wiring between the instrument and the coupons.

The sense voltages from the coupons 33 and 35 respectively, are supplied to instrumentation amplifiers 41 and 43, which in practice are U3a and U3b. These amplifiers have very low noise and very low DC offset. Low DC offset is necessary to keep the amplifiers out of saturation, given the high gain and the low supply voltage available. The amplifiers 41 and 43 are set to a gain of 1000 (60 dB). They are arranged such that the phase-opposite voltages from coupons 27 and 37 are amplified in phase to minimize crosstalk, although crosstalk isolation between amplifiers 41 and 43 exceeds 120 dB.

The outputs of the instrumentation amplifiers 41 and 43 are AC-coupled to post amplifiers 45 and 47 respectively, or U4a and U5a respectively. AC coupling is used to remove any amplified DC offset error from the instrumentation amps.

The post-amplified signals are presented to precision full wave rectifiers 49 and 51 respectively, comprised of U4b and U5b and associated circuitry. The theory of operation of this block is straightforward and well documented by those skilled in the art.

The resulting full-wave rectified signals are low-pass filtered via filters 53 and 55 (U4c and U5c) respectively, using $2^{nd}$ order Butterworth-response filters comprised of U4d for one channel and U5d for the other channel. These are Sallen-Key filters with unity gain regardless of tolerance in resistor values. These filters 53 and 55 have a 3 dB corner frequency of 5 Hz. This form of filtering has been found to be superior over conventional R-C post-detection filtering to achieve fast response with good rejection of post-rectification ripple. Their DC output is proportional to the average value of the rectified AC input. It is settled to within 0.2% within 200 milliseconds of oscillator startup, including delay in the oscillator filter. At 1 volt output, ripple is about 500 μV RMS.

Filters 53 and 55 limit system bandwidth to 5 Hz, which gives the system very good immunity to electromagnetic interference and to Johnson noise in the low-level stages.

The inputs are protected against transients by resistors 57 and 59, followed by diode clamps 61 to ground 63 and Vcc. DC offset from leakage currents of the diode 61 is negligible over the full military temperature range due to the low impedances involved. In addition, the instrumentation op amps used are internally protected for overvoltage up to 40 volts.

U6 is a charge-pump voltage inverter operating at about 35 KHz to produce a negative bias voltage for the instrumentation op amps. The input signals are within less than a millivolt of ground potential so the first stage amplifiers require negative bias. Power supply rejection of these amplifiers exceeds 120 dB at the frequencies of interest and the 5 Hz low pass filter 15 will eliminate any noise significantly above that frequency, so the negative bias is not regulated.

Output 1 and output 2 produce signals that are compared to determine the degree of corrosion measured by the system of this invention. The test sample output, 75 and the reference sample output 77 are both representative of the condition of the respective coupons or samples. Electrical resistance is directly related to the degree of corrosion, based on the formula R=ρL/A, where R is electrical resistance, ρ is the resistivity of the material, L is the element's length, and A is the cross sectional area of the element. The outputs 75 and 77 are compared and the difference in surface area calculated represents the degree of corrosion. In the present invention, the current driving the reference and sensor coupons, in series as shown in FIGS. 1 and 2, uses a ratiometric measurement such that the ratio of the outputs is an accurate measurement of the degree of corrosion. Tests show that on site measurement of corrosion using the present invention corresponds with data from physical measurements of corrosion using weight-loss calculations. The present invention operates in situ, and does not require removal of the sample to determine the degree of corrosion. Not only is the present invention useable on site, on a continuous basis, it consumes low power, thus allowing for battery operation over long periods of time.

While particular embodiments of the present invention have been illustrated and described, they are merely exemplary and a person skilled in the art may make variations and modifications to the embodiments described herein without departing from the spirit and scope of the present invention. All such equivalent variations and modifications are intended to be included within the scope of this invention, and it is not intended to limit the invention, except as defined by the following claims.

The invention claimed is:

1. A system for monitoring corrosion in metal, comprising:
   a test sample exposed to a corrosion causing environment and a reference sample exposed to a protected environment;
   an AC voltage source adapted to generate a square wave signal oscillating between ground and voltage Vcc;
   a filter positioned to receive said signal and filter said signal to produce a sine wave with no second harmonic component;
   a voltage-driven current source and inverting amplifier adapted to receive said sine wave and produce a current referenced to 0.5 Vcc to provide an AC current from the drive voltage driven sinusoidally and symmetrically above and below 0.5 Vcc;
   a transformer for receiving said AC current and stepping up said AC current and thereafter transmit said stepped up current through said test sample and said reference sample in series connection; and
   an amplifier for amplifying AC voltage that is the result of said AC current and respective resistances of test sample and said reference sample to provide a test output and a reference output voltage in a ratio representing the degree of corrosion of said reference sample.

2. The system of claim 1, where said square wave signal operates at a frequency ranging from about 50 Hz to about 150 Hz.

3. The system of claim 2, where said frequency is about 100 Hz.

4. The system of claim 1, where said transformer operates at a current step up ratio of from about 5:1 to about 15:1.

5. The system of claim 1, where said transformer operates at a current step up ratio of about 10:1.

6. The system of claim 1, wherein said amplifier is a pair of amplifiers in series and each is adapted to amplify one of said test output and sample output by an identical gain of from about 500 to about 2000.

7. The system of claim 6, wherein said gain is about 1000.

8. The system of claim 1, which further includes full-wave rectifiers for rectifying said amplified test output signal and said reference output signal to produce rectified amplified signals.

9. The system of claim 1, which further includes low pass filters for filtering said rectified amplified signals prior to use of said signals to calculate the degree of corrosion of said output signals.

10. The system of claim 1, wherein said test output and a reference output voltage ratio representing the degree of corrosion of said reference sample is measured in situ.

11. A system for monitoring corrosion in metal, comprising:
    a test sample exposed to a corrosion causing environment and a reference sample exposed to a protected environment;
    AC voltage source means for generating a square wave signal oscillating between ground and voltage Vcc;
    filter means for receiving said signal and filter said signal to produce a sine wave with no second harmonic component;
    voltage-driven current source means and inverting amplifier means adapted to receive said sine wave for producing a current referenced to 0.5 Vcc to provide an AC current from the drive voltage driven sinusoidally and symmetrically above and below 0.5 Vcc;
    transformer means for receiving said AC current and stepping up said AC current and thereafter transmit said stepped up current through said test sample and said reference sample in series connection; and
    amplifier means for amplifying the AC voltage that is the result of said AC current and respective resistances of test sample and said reference sample to provide a test output and a sample output voltage in a ratio representing the degree of corrosion of said reference sample.

12. The system of claim 11, where said square wave signal operates at a frequency ranging from about 50 Hz to about 150 Hz.

13. The system of claim 12, where said frequency is about 100 Hz.

14. The system of claim 11, where said transformer operates at a current step up ratio of from about 5:1 to about 15:1.

15. The system of claim 14, where said transformer operates at a current step up ratio of about 10:1.

16. The system of claim 11, wherein said amplifier is a pair of amplifiers in series and each is adapted to amplify one of said test output and sample output by an identical gain of from about 500 to about 2000.

17. The system of claim 16, wherein said gain is about 1000.

18. The system of claim 11, which further includes full-wave rectifiers for rectifying said amplified test output signal and said reference output signal to produce rectified amplified signals.

19. The system of claim 11, which further includes low pass filters for filtering said rectified amplified signals prior to use of said signals to calculate the degree of corrosion of said output signals.

20. The system of claim 11, wherein said test output and a reference output voltage ratio representing the degree of corrosion of said reference sample is measured in situ.

* * * * *